United States Patent
Tanaka et al.

(10) Patent No.: US 9,883,126 B2
(45) Date of Patent: Jan. 30, 2018

(54) IMAGE PICKUP DEVICE AND METHOD

(71) Applicant: FUJIFILM Corporation, Tokyo (JP)

(72) Inventors: Yasutake Tanaka, Kanagawa (JP); Hiromi Ishikawa, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 43 days.

(21) Appl. No.: 15/176,306

(22) Filed: Jun. 8, 2016

(65) Prior Publication Data

US 2017/0013212 A1   Jan. 12, 2017

(30) Foreign Application Priority Data

Jul. 8, 2015  (JP) ................................ 2015-136628

(51) Int. Cl.
*H04N 5/357* (2011.01)
*G01N 21/64* (2006.01)
*G01N 21/76* (2006.01)
*G02B 3/00* (2006.01)
*G02B 3/06* (2006.01)
(Continued)

(52) U.S. Cl.
CPC ....... *H04N 5/3572* (2013.01); *G01N 21/6456* (2013.01); *G01N 21/76* (2013.01); *G02B 3/005* (2013.01); *G02B 3/0062* (2013.01); *G02B 3/06* (2013.01); *G02B 26/0875* (2013.01); *H01L 27/14627* (2013.01); *H04N 1/19* (2013.01)

(58) Field of Classification Search
CPC .................................................. H04N 5/3572
See application file for complete search history.

(56) References Cited

U.S. PATENT DOCUMENTS 6,545,811 B1 *  4/2003  Fujimoto ............. G02B 3/0031
                                                                359/619
2002/0036255 A1 *  3/2002  Ogi ........................ B41J 2/451
                                                                250/208.1

(Continued)

FOREIGN PATENT DOCUMENTS

| JP | 1-94775 A | 4/1989 |
|---|---|---|
| JP | 2010-187214 A | 8/2010 |
| WO | 99/40471 A1 | 8/1999 |

OTHER PUBLICATIONS

Communication dated Jan. 18, 2017 from the European Patent Office in counterpart Application No. 16173285.4.

*Primary Examiner* — Roberto Velez
*Assistant Examiner* — Cynthia Segura
(74) *Attorney, Agent, or Firm* — Sughrue Mion, PLLC

(57) ABSTRACT

In an image pickup device and method using a lens unit in which a plurality of lens arrays, are arranged and a lens holding unit is provided between the lens arrays, light emitted from the area corresponding to the lens holding unit can be detected. A moving mechanism that moves a lens unit or the observation target holding unit and the detection unit, and a moving mechanism control unit are provided. The moving mechanism control unit controls the moving mechanism such that the lens unit or the observation target holding unit and the detection unit are moved to a second position from a first position. The second position is set to a position when the lens array after the movement is disposed at a position facing the detection surface of the detection unit shielded by a lens holding unit when the lens unit is disposed at the first position.

20 Claims, 8 Drawing Sheets

(51) Int. Cl.
*G02B 26/08* (2006.01)
*H01L 27/146* (2006.01)
*H04N 1/19* (2006.01)

(56) References Cited

U.S. PATENT DOCUMENTS

| | | | | |
|---|---|---|---|---|
| 2012/0200899 A1* | 8/2012 | Ogi | ................ | G02B 3/0062 |
| | | | | 358/475 |
| 2015/0053844 A1* | 2/2015 | Kitamura | ................ | G02B 3/005 |
| | | | | 250/208.1 |
| 2015/0109676 A1* | 4/2015 | Kobayashi | ................ | G02B 3/0006 |
| | | | | 359/619 |
| 2016/0152039 A1* | 6/2016 | Suzuki | ................ | B41J 2/451 |
| | | | | 347/258 |
| 2016/0291215 A1* | 10/2016 | Suzuki | ................ | G02B 3/0075 |

* cited by examiner

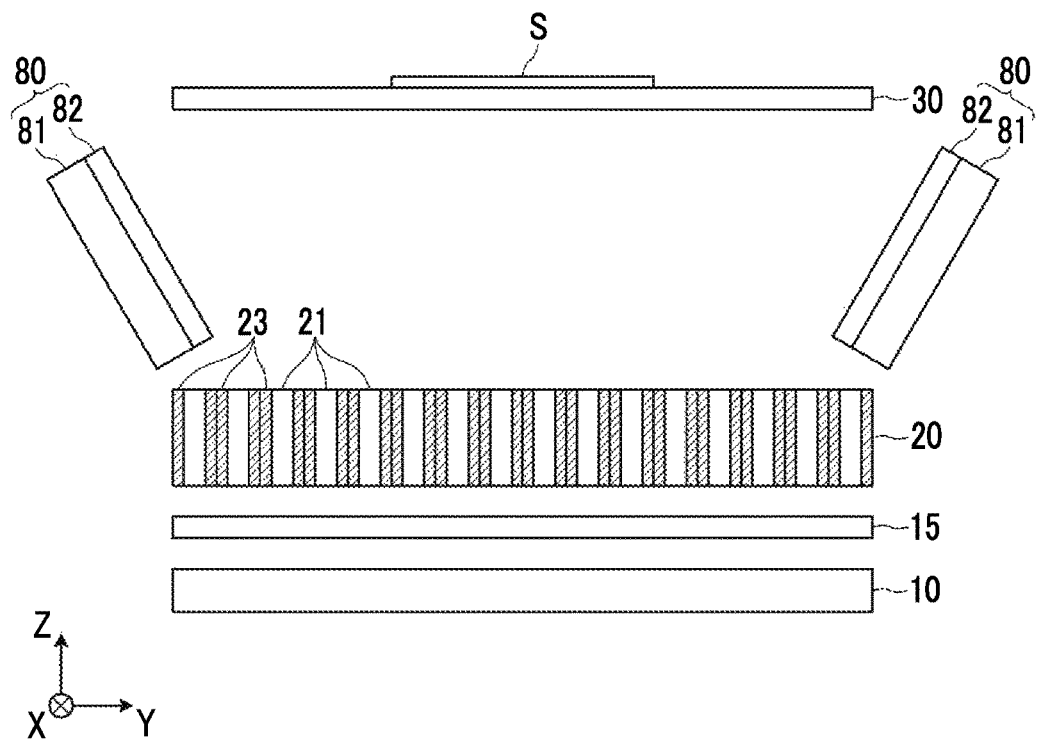
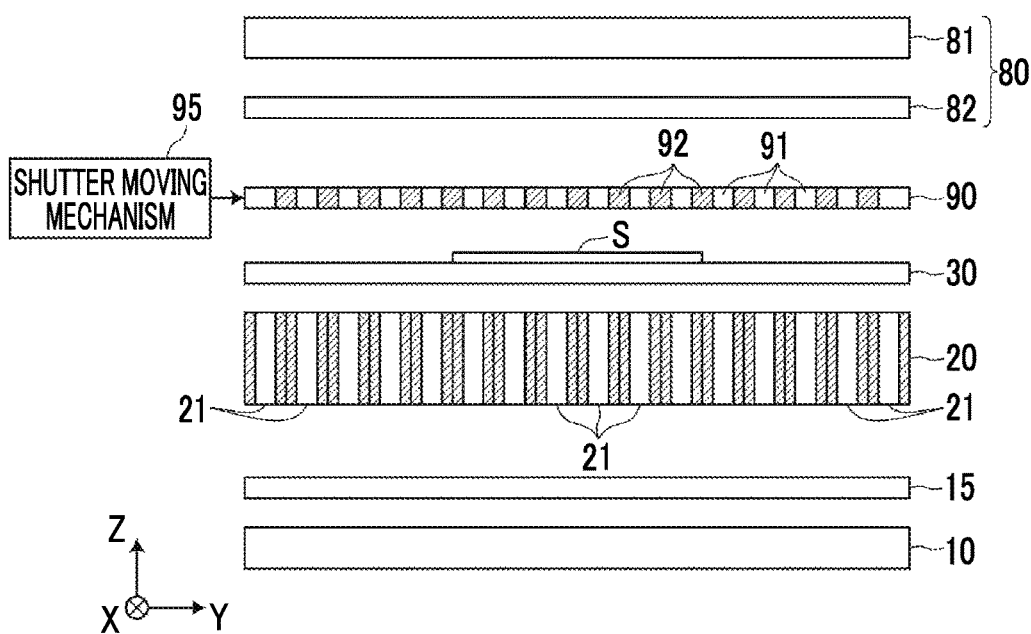

IMAGE PICKUP DEVICE AND METHOD

CROSS-REFERENCE TO RELATED APPLICATIONS

The present application claims priority under 35 U.S.C. § 119 to Japanese Patent Application No. 2015-136628, filed on Jul. 8, 2015. Each of the above application(s) is hereby expressly incorporated by reference, in its entirety, into the present application.

BACKGROUND OF THE INVENTION

1. Field of the Invention

The present invention relates to an image pickup device and method for detecting light, which is emitted from an observation target held by an observation target holding unit, using a detection unit in which detection elements are arranged in a two-dimensional manner.

2. Description of the Related Art

In the related art, chemiluminescence or fluorescence emitted from an observation target is photoelectrically detected by detection elements, and an image is displayed based on the detection signal. As a method of detecting the chemiluminescence or fluorescence, for example, there is a method of scanning an observation target by moving a one-dimensional detection unit, in which detection elements are arranged in a one-dimensional manner, in a direction perpendicular to the arrangement direction of the detection elements. In this case, it is possible to use a contact image sensor or the like.

However, in the case of detecting chemiluminescence by performing a scan using a one-dimensional detection unit as described above, chemiluminescence may fade before the end after the start of scanning by the one-dimensional detection unit. This is not preferable since image unevenness can be caused.

Therefore, detecting chemiluminescence or fluorescence using a two-dimensional detection unit, in which detection elements are arranged in a two-dimensional manner, instead of the one-dimensional detection unit described above, can be considered.

SUMMARY OF THE INVENTION

However, in the case of using a two-dimensional detection unit as described above, protection of the two-dimensional detection unit and blurring of an image become problems. Specifically, for example, in a case where an observation target is directly placed on the detection surface of the two-dimensional detection unit and light emitted from the observation target is detected, there is a risk that the detection surface will be damaged by contact between the detection surface of the two-dimensional detection unit and the observation target.

Therefore, providing a protective member, which holds an observation target and protects the detection surface of the two-dimensional detection unit, between the two-dimensional detection unit and the observation target can be considered. However, in a case where such a protective member is provided, light emitted from the observation target reaches the two-dimensional detection unit through the protective member. Accordingly, there is a problem that an image detected by the two-dimensional detection unit is blurred.

As a method of locating the observation target and the two-dimensional detection unit away from each other and preventing blurring of an image detected by the two-dimensional detection unit, for example, providing an imaging optical system, such as a lens array in which fiber optics or refractive index distribution type lenses are arranged, between the observation target and the two-dimensional detection unit can be considered.

However, since fiber optics are so expensive, there is a problem that the cost is increased. In contrast, a lens array in which refractive index distribution type lenses are arranged is not as expensive as fiber optics. Accordingly, the influence of cost increase is small.

However, in the case of detecting light emitted from the observation target using the two-dimensional detection unit as described above, a lens array in which refractive index distribution type lenses are arranged in a two-dimensional manner is required, but there is generally only a linear lens array as a commercially available lens array.

Accordingly, it is necessary to arrange a plurality of linear lens arrays in a direction perpendicular to the longitudinal direction. In a general lens array commercially available, however, lens holding units that hold a row of refractive index distribution type lenses therebetween are provided. Since the lens holding unit is formed of black resin or the like, light cannot pass through the lens holding unit. That is, in a case where a plurality of lens arrays having such lens holding units are arranged, light emitted from the area of the observation target corresponding to the lens holding units is blocked by the lens holding units. Accordingly, there is a problem that the light cannot be detected by the two-dimensional detection unit.

JP 1989-094775A (JP-H01-094775A) and JP2010-187214A propose apparatuses that detect an image of an observation target using refractive index distribution type lenses that are arranged in a two-dimensional manner, but a method of solving the blocking of light due to the lens holding unit described above is not disclosed.

In view of the aforementioned problem, it is an object of the invention to provide an image pickup device and method capable of detecting light emitted from the area of an observation target corresponding to lens holding units and of capturing an appropriate image without image blurring.

An image pickup device of the invention comprises: an observation target holding unit that holds an observation target; a detection unit in which detection elements for detecting light emitted from the observation target are arranged in a two-dimensional manner; a lens unit which is disposed between the observation target holding unit and the detection unit and in which a plurality of lens arrays, each of which includes a plurality of refractive index distribution type lenses that are linearly arranged, are arranged in a direction perpendicular to an arrangement direction of the refractive index distribution type lenses and a lens holding unit that blocks the light is provided between the lens arrays; a moving mechanism that moves the lens unit or the observation target holding unit and the detection unit in the perpendicular direction; and a moving mechanism control unit that controls the moving mechanism. The moving mechanism control unit controls the moving mechanism such that the lens unit or the observation target holding unit and the detection unit are moved to a second position from a first position. The second position is a position when the lens array of the lens unit after the movement is disposed at a position facing a detection surface of the detection unit shielded by the lens holding unit when the lens unit is disposed at the first position.

In the image pickup device of the invention described above, it is preferable that a moving distance from the first position to the second position is shorter than a distance between center axes of the lens arrays disposed adjacent to each other in the perpendicular direction.

In the image pickup device of the invention described above, a plurality of second positions may be set in the perpendicular direction.

The image pickup device of the invention described above may further comprise an image forming unit that forms one image by superimposing a first image detected at the first position by the detection unit and a second image detected at the second position by the detection unit.

In the image pickup device of the invention described above, the moving mechanism control unit may move the lens unit or the observation target holding unit and the detection unit to the second position from the first position during a single exposure time set in advance.

In the image pickup device of the invention described above, the moving mechanism control unit may make the lens unit or the observation target holding unit and the detection unit reciprocate between the first and second positions during the single exposure time.

The image pickup device of the invention described above may further comprise an excitation light emission unit that emits excitation light to the observation target, and the detection unit may detect fluorescence emitted from the observation target due to emission of the excitation light.

The image pickup device of the invention described above may further comprise an excitation light filter that is provided between the excitation fight emission unit and the observation target holding unit and that transmits light in a wavelength range set in advance, which includes a center wavelength of the excitation light, and inhibits transmission of light having a wavelength outside the wavelength range.

The image pickup device of the invention described above may further comprise an excitation light cut filter that is provided between the observation target holding unit and the detection unit and inhibits incidence of the excitation light to the detection unit.

The image pickup device of the invention described above may further comprise a shutter unit which is provided between the excitation light emission unit and the observation target and in which openings are provided at intervals corresponding to a distance between center axes of the lens arrays for a light shielding member for blocking the excitation light.

The image pickup device of the invention described above may further comprise a shutter moving mechanism that moves the shutter unit in the perpendicular direction, and the moving mechanism control unit may control the shutter moving mechanism such that the shutter unit is moved in synchronization with movement of the lens unit.

The image pickup device of the invention described above may further comprise a shutter control unit that switches positions of the openings of the shutter unit in synchronization with movement of the lens unit.

In the image pickup device of the invention described above, the excitation light emission unit may stop emission of the excitation light during movement of the lens unit or the observation target holding unit and the detection unit.

An image pickup method of the invention is an image pickup method of detecting light emitted from an observation target held by an observation target holding unit using a detection unit including detection elements arranged in a two-dimensional manner. The image pickup method comprises moving a lens unit, which is disposed between the observation target holding unit and the detection unit and in which a plurality of lens arrays, each of which includes a plurality of refractive index distribution type lenses that are linearly arranged, are arranged in a direction perpendicular to an arrangement direction of the refractive index distribution type lenses and a lens holding unit that blocks the light is provided between the lens arrays, or the observation target holding unit and the detection unit in the perpendicular direction such that the lens unit or the observation target holding unit and the detection unit are moved to a second position from a first position. The second position is a position when the lens array of the lens unit after the movement is disposed at a position facing a detection surface of the detection unit shielded by the lens holding unit when the lens unit is disposed at the first position.

According to the image pickup device and method of the invention, the lens unit in which a plurality of lens arrays, each of which includes a plurality of refractive index distribution type lenses that are linearly arranged, are arranged in a direction perpendicular to the arrangement direction and the lens holding unit that blocks light is provided between the lens arrays is disposed between the observation target holding unit and the detection unit. In addition, the lens unit or the observation target holding unit and the detection unit are moved in the perpendicular direction so as to be moved from the first position to the second position.

In addition, the second position is set to a position when the lens array of the lens unit after the movement is disposed at a position facing the detection surface of the detection unit shielded by the lens holding unit when the lens unit is disposed at the first position. Therefore, since it is also possible to detect light emitted from the area of the observation target corresponding to the lens holding unit, it is possible to capture an appropriate image without image blurring.

BRIEF DESCRIPTION OF THE DRAWINGS

FIG. 11 is a diagram showing the schematic configuration of another embodiment to detect the fluorescence of an observation target.

FIG. 12 is a diagram showing the schematic configuration of an embodiment to detect the fluorescence emitted from a phosphor sheet including a stimulable phosphor layer.

DESCRIPTION OF THE PREFERRED EMBODIMENTS

Figure 1:
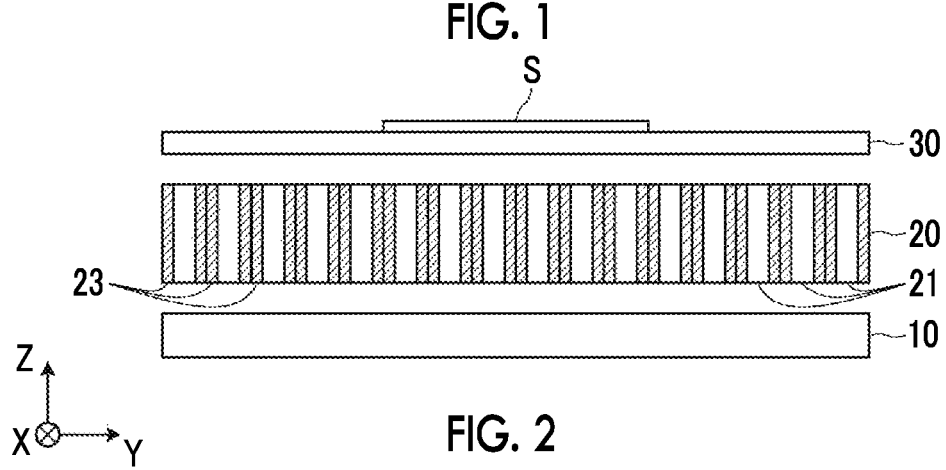
FIG. 1 is a diagram showing the schematic configuration of an image pickup device main body in an image pickup system using an embodiment of an image pickup device of the invention.

Hereinafter, an image pickup system using an embodiment of an image pickup device and method of the invention will be described in detail with reference to the accompanying diagrams. The image pickup system of the present embodiment includes an image pickup device main body and an image pickup control device that controls the image pickup device main body. FIG. 1 is a diagram showing the schematic configuration of the image pickup device main body in the image pickup system of the present embodiment.

As shown in FIG. 1, the image pickup device main body of the present embodiment includes a detection unit 10, a lens unit 20, and an observation target holding unit 30. In the present embodiment, the image pickup device of the invention is formed by the detection unit 10, the lens unit 20, and the observation target holding unit 30 shown in FIG. 1, a moving mechanism 40 shown in FIG. 4, and a moving mechanism control unit 52 shown in FIG. 7.

The observation target holding unit 30 holds an observation target S. Specifically, the observation target holding unit 30 is formed of a material, such as glass or resin allowing light emitted from the observation target S to be transmitted therethrough, and is formed in the shape of a flat plate having a mounting surface on which the observation target S is placed. Examples of light emitted from the observation target S include chemiluminescence, fluorescence, and the like.

Figure 2:
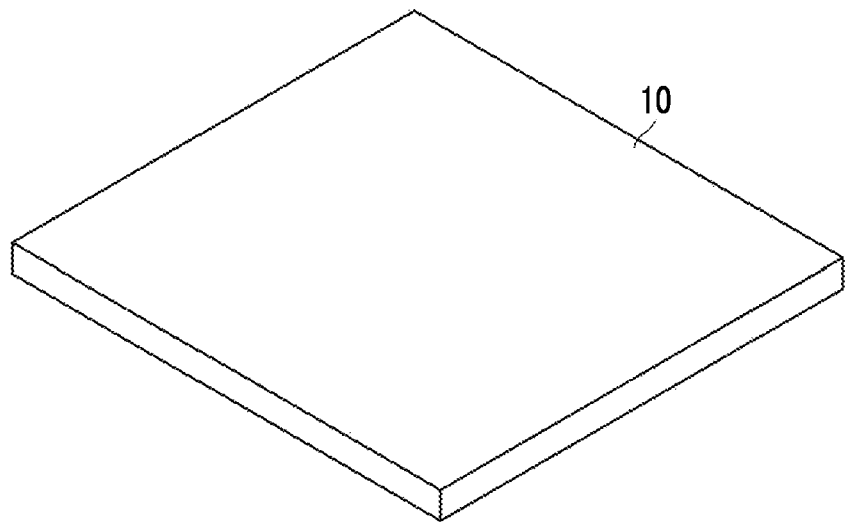
FIG. 2 is a perspective view schematically showing a detection unit.

In the detection unit 10, detection elements that detects light, which is emitted from the observation target S and is transmitted through the observation target holding unit 30 and the lens unit 20, are arranged in a two-dimensional manner. FIG. 2 is a perspective view schematically showing the detection unit 10. As shown in FIG. 2, the detection unit 10 has a rectangular detection surface. Specifically, for example, a flat panel detector (FPD), a charge-coupled device (CCD) type detector, and a complementary metal-oxide semiconductor (CMOS) type detector can be used. As the size of each detection element (pixel) that forms the detection unit 10, for example, about 50 µm square to 100 µm square can be set. As the size of the detection unit 10, for example, 10 cm×10 cm or more can be set. However, the size of the detection unit 10 can be appropriately changed according to the size of the observation target S or the like.

Figure 3:
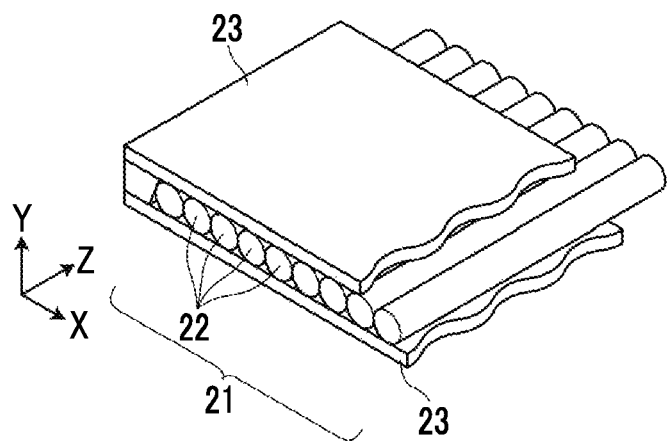
FIG. 3 is a perspective view showing the schematic configuration of a SELFOC (registered trademark) lens array.

The lens unit 20 is disposed between the observation target holding unit 30 and the detection unit 10, and includes an array 21 of a plurality of SELFOC (registered trademark; the same hereinbelow) lenses (corresponding to a lens array of the invention). FIG. 3 is a perspective view showing the schematic configuration of the SELFOC lens array 21. As shown in FIG. 3, in the SELFOC lens array 21, a plurality of SELFOC lenses 22 (corresponding to a refractive index distribution type lens of the invention) are linearly arranged.

As the SELFOC lens array 21, for example, an array in which the lens diameter of the SELFOC lens 22 is about 0.1 mm to 5 mm can be used.

As shown in FIG. 3, lens holding units 23 that hold the SELFOC lens 22 are provided on both side surfaces of the SELFOC lenses 22 that are linearly arranged. The lens holding unit 23 is formed in a flat plate shape, and is formed of a member that blocks light emitted from the observation target S. For example, the lens holding unit 23 is formed of black resin. In the present embodiment, an array obtained by arranging a row of SELFOC lenses 22 is used as the SELFOC lens array 21. However, the invention is not limited thereto, and an array obtained by arranging two or more rows of SELFOC lenses so as to be interposed between the lens holding units 23 described above may be used.

In the lens unit 20, a plurality of SELFOC lens arrays 21 shown in FIG. 3 are arranged in a direction (Y direction shown in FIG. 3) perpendicular to the arrangement direction (X direction shown in FIG. 3) of the SELFOC lenses 22.

In the image pickup device main body, the detection unit 10, the lens unit 20, and the observation target holding unit 30 are disposed at predetermined distances therebetween in a Z direction (extending direction of each SELFOC lens 22) perpendicular to the X and Y directions, as shown in FIG. 1. The distances between the detection unit 10, the lens unit 20, and the observation target holding unit 30 are set by the focal length of the SELFOC lens array 21.

Figure 4:
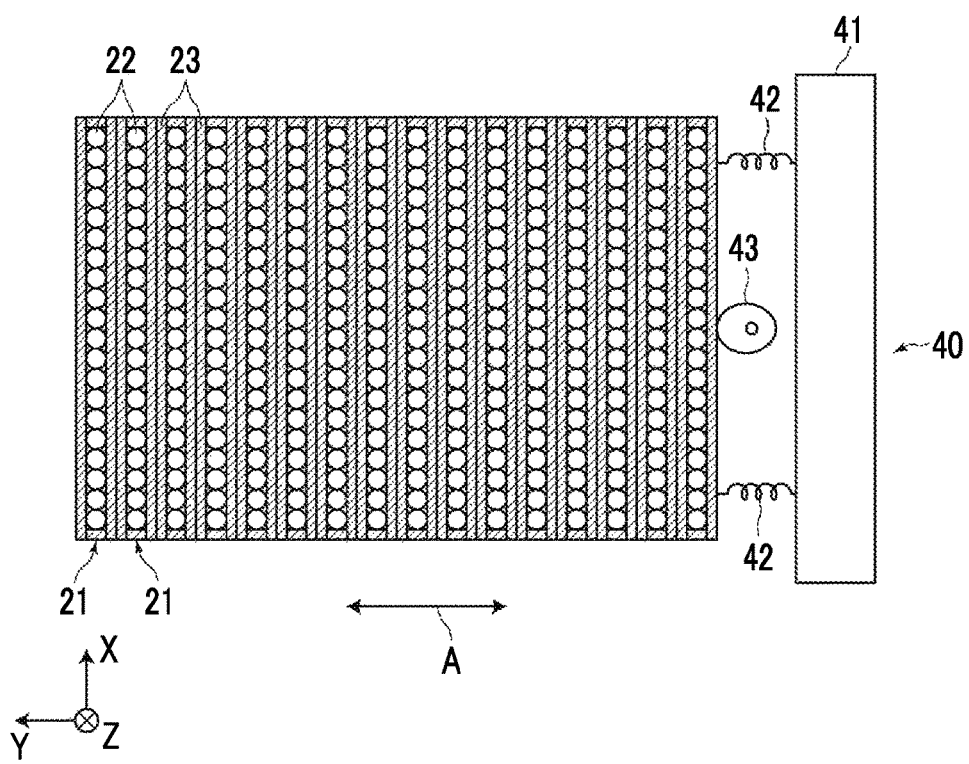
FIG. 4 is a top view of a lens unit, and is a diagram showing the schematic configuration of a moving mechanism.

In addition, as shown in FIG. 4, the image pickup device main body includes the moving mechanism 40 that moves the lens unit 20 in a direction (Y direction shown in FIG. 4) perpendicular to the arrangement direction of the SELFOC lens 22. As shown in FIG. 4, the moving mechanism 40 includes a support member 41, a spring member 42, and a cam 43. One end of the spring member 42 is connected to the support member 41, and the other end is connected to the lens unit 20. The cam 43 and the side surface of the lens unit 20 parallel to the X direction are disposed so as to be in contact with each other, and the lens unit 20 is moved in the Y direction by the rotation of the cam 43.

Figure 5:
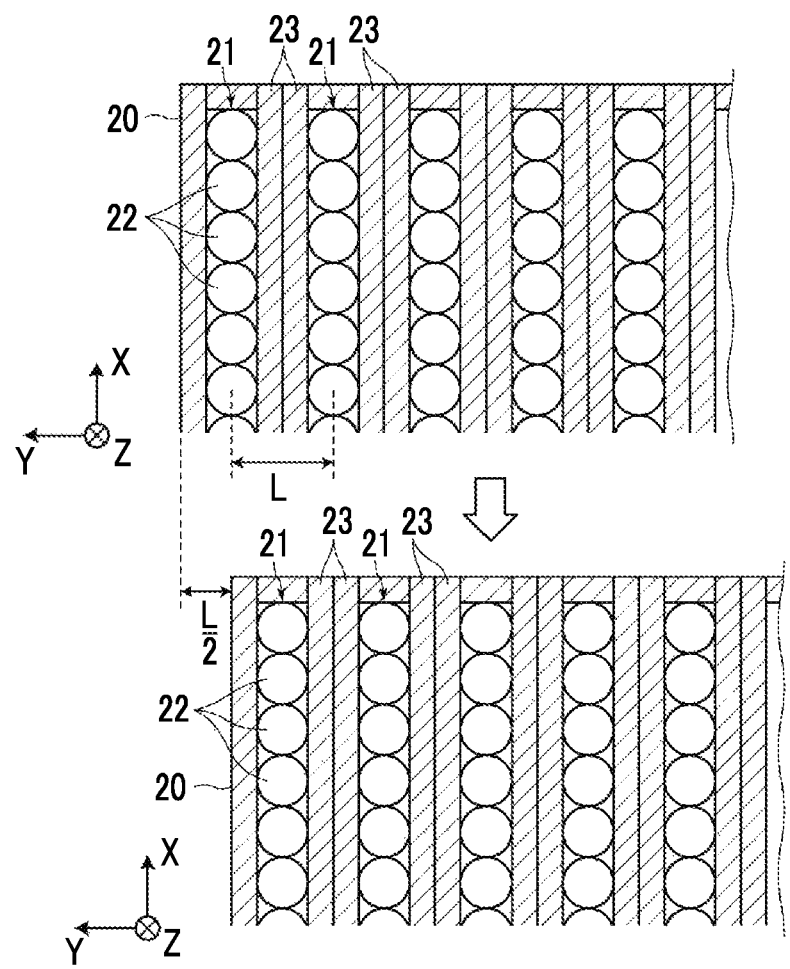
FIG. 5 is a diagram illustrating the movement from the first position to the second position of the lens unit.

Here, the moving distance of the lens unit 20 will be described with reference to FIG. 5.

The moving mechanism 40 moves the lens unit 20 from a first position to a second position. An upper diagram in FIG. 5 shows the first position, and a lower diagram in FIG. 5 shows the second position. The second position is a position when the SELFOC lens array 21 of the lens unit 20 after the movement is disposed at a position facing the detection surface of the detection unit 10 shielded by the lens holding unit 23 when the lens unit 20 is disposed at the first position.

Specifically, in the present embodiment, the moving distance from the first position to the second position is set to a distance L/2 that is the half of a distance L between the center axes in the Y direction of the SELFOC lens arrays 21 disposed adjacent to each other in the Y direction. In the present embodiment, it is preferable that the length of the lens holding unit 23 in the Y direction is equal to or less than the diameter of the SELFOC lens 22. However, in a case where the field of view of the SELFOC lens 22 in the Y direction is wider than the length of the lens holding unit 23 in the Y direction, the length of the lens holding unit 23 in the direction may be larger than the diameter of the SELFOC lens 22.

Figure 6:
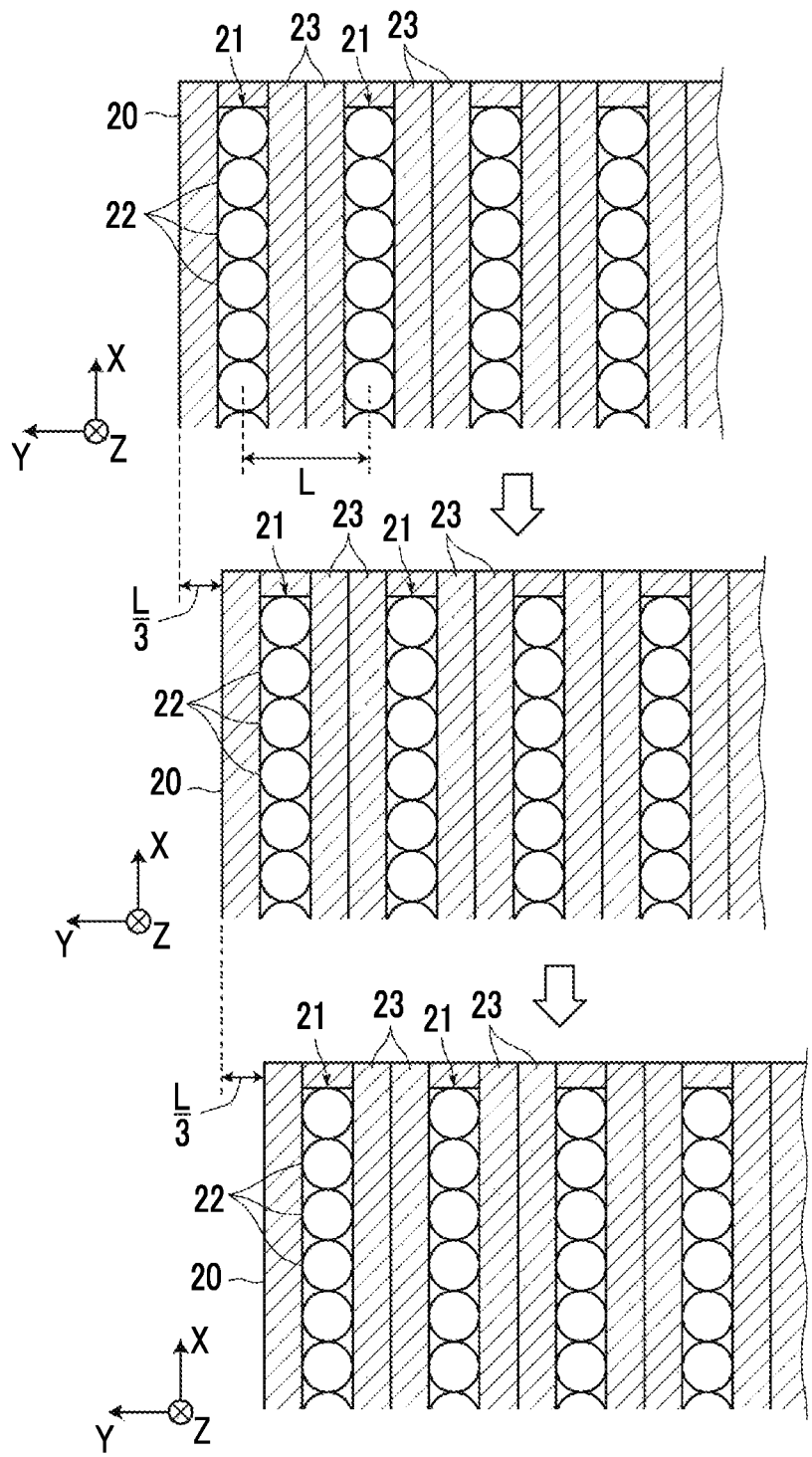
FIG. 6 is a diagram illustrating a case where a plurality of second positions are set.

In a case where the length of the lens holding unit 23 in the Y direction is larger than the diameter of the SELFOC lens 22 or the field of view of the SELFOC lens 22 in the Y direction, a plurality of second positions may be set. FIG. 6 shows an example in a case where a plurality of second positions are set. FIG. 6 shows a case where two positions are set as the second position. Here, the two positions are referred to as a third position and a fourth position. An upper diagram in FIG. 6 shows the first position, a middle diagram in FIG. 6 shows the third position, and a lower diagram in FIG. 6 shows the fourth position. The third and fourth positions are also positions when the SELFOC lens array 21 of the lens unit 20 after the movement is disposed at a position facing the detection surface of the detection unit 10 shielded by the lens holding unit 23 when the lens unit 20 is disposed at the first position.

Specifically, in the present embodiment, the moving distance from the first position to the third position and the moving distance from the third position to the fourth position are set to a distance L/3 that is ⅓ of the distance L between the center axes in the Y direction of the SELFOC lens arrays 21 disposed adjacent to each other in the Y direction.

Although two positions are set as the second position in the example shown in FIG. 6, three or more positions may be set as the second position according to the length of the lens holding unit 23 in the Y direction or the field of view of the SELFOC lens 22 in the Y direction.

In the present embodiment, as the SELFOC lens array 21, an array in which the SELFOC lenses 22 are arranged in a row is used. However, for example, also in a case where an array, in which the SELFOC lenses 22 are arranged in a plurality of rows in the Y direction, is used as the SELFOC lens array 21, the moving distance of the lens unit 20 may be set to ½ or ⅓ of the distance L between the center axes in the Y direction of the SELFOC lens arrays 21 disposed adjacent to each other in the Y direction. In a case where an array in which the SELFOC lenses 22 are arranged in a plurality of rows in the Y direction is used as the SELFOC lens array 21 as described above, the center axis of the SELFOC lens array 21 refers to a middle position between the center axes of the rows of the SELFOC lenses disposed at both ends in the Y direction.

In addition, in the present embodiment, the moving mechanism 40 is configured to include the support member 41, the spring member 42, and the cam 43. However, the configuration of the moving mechanism 40 is not limited to the above configuration, and any configuration capable of moving the lens unit 20 in the Y direction may be adopted. For example, a piezoelectric material may be used instead of the cam 43. Specifically, instead of the cam 43, a piezoelectric actuator formed of a piezoelectric material may be provided on the side surface of the lens unit 20 parallel to the X direction. By driving the piezoelectric actuator by supplying a driving voltage from the moving mechanism control unit 52 to the piezoelectric actuator, the lens unit 20 may be moved in the Y direction.

Figure 7:
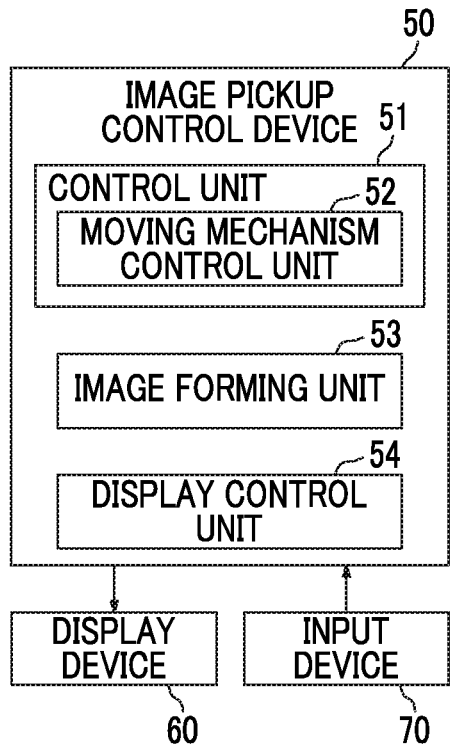
FIG. 7 is a block diagram showing the schematic configuration of an image pickup control device in the image pickup system using an embodiment of the image pickup device of the invention.

FIG. 7 is a block diagram showing the schematic configuration of an image pickup control device 50. The image pickup control device 50 controls the image pickup device main body, and is a computer including a central processing unit (CPU) or a storage device. The image pickup control device 50 includes a control unit 51, an image forming unit 53, and a display control unit 54. The control unit 51 controls the entire image pickup device including the detection unit 10. In particular, the control unit 51 includes the moving mechanism control unit 52 that controls the moving mechanism 40.

The image forming unit 53 forms one image by superimposing a first image detected at the first position by the detection unit 10 and a second image detected at the second position by the detection unit 10.

The display control unit 54 displays the image formed by the image forming unit 53 on a display device 60.

An input device 70 and the display device 60 are connected to the image pickup device main body. The input device 70 includes an input device, such as a keyboard or a mouse, and receives a setting input from the user.

The display device 60 is a display device, such as a liquid crystal display, and displays an image formed by the image forming unit 53 or the like. In addition, by forming the display device 60 using a touch panel so that the setting input is possible by the pressing of the screen, the display device 60 may also serve as an input device.

Figure 8:
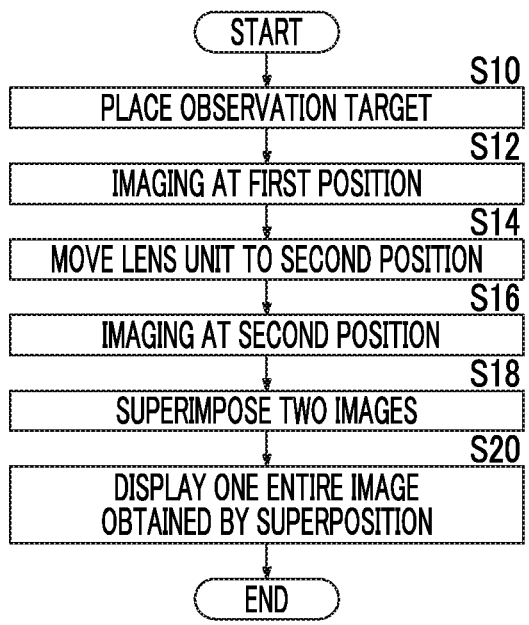
FIG. 8 is a flowchart illustrating the operation of the image pickup system using an embodiment of the image pickup device of the invention.

Next, the operation of the image pickup system of the present embodiment will be described with reference to the flowchart shown in FIG. 8.

First, the observation target S is placed on the observation target holding unit 30 (S10). Then, the user inputs an imaging start instruction using the input device 70, so that imaging is started.

Specifically, exposure of the detection unit 10 is started in a state in which the lens unit 20 is placed at the first position, light transmitted through the SELFOC lens array 21 of the lens unit 20 is detected by the detection unit 10, and the exposure is ended after the passage of exposure time set in advance, so that the imaging at the first position is performed (S12). At this time, light emitted to the lens holding unit 23 of the lens unit 20, among light components emitted from the observation target S, is absorbed by the lens holding unit 23. Accordingly, no light is detected in the area of the detection surface of the detection unit 10 corresponding to the area of the lens holding unit 23.

The first image detected by imaging in a state in which the lens unit 20 is provided at the first position is read from the detection unit 10 in response to a control signal from the control unit 51, and is stored in the image forming unit 53.

Then, the cam 43 of the moving mechanism 40 rotates in response to a control signal output from the moving mechanism control unit 52, and accordingly, the lens unit 20 moves in the Y direction to move to the second position (S14).

Then, exposure of the detection unit 10 is started in a state in which the lens unit 20 is placed at the second position, light transmitted through the SELFOC lens array 21 of the lens unit 20 is detected by the detection unit 10, and the exposure is ended after the passage of exposure time set in advance, so that the imaging at the second position is performed (S16). Also in the imaging at the second position, light emitted to the lens holding unit 23 of the lens unit 20 among light components emitted from the observation target S is absorbed by the lens holding unit 23, and no light is detected in the area of the detection surface of the detection unit 10 corresponding to the area of the lens holding unit 23. The second image detected by imaging in a state in which the lens unit 20 is provided at the second position is read from the detection unit 10 in response to a control signal from the control unit 51, and is stored in the image forming unit 53.

The image forming unit 53 forms one entire image of the observation target S by superimposing the first and second images so that the imaging area of the observation target S in the first image and the imaging area of the observation target S in the second image are alternately arranged (S18).

The entire image formed by the image forming unit 53 is output to the display control unit 54, and the display control unit 54 displays the entire image of the observation target S on the display device 60.

According to the image pickup system of the above-mentioned embodiment, a plurality of SELFOC lens arrays 21 are arranged in which a plurality of SELFOC lenses 22 are linearly arranged, the lens unit 20 having the lens holding unit 23 for blocking light between the SELFOC lens arrays 21 is disposed between the observation target holding unit 30 and the detection unit 10, and the lens unit 20 is made to move from the first position to the second position. Therefore, since light emitted from the area of the observation target S corresponding to the lens holding unit 23 can also be detected, it is possible to capture an appropriate image without image blurring.

In addition, in the image pickup system of the embodiment described above, the exposure time of the first image captured in a state in which the lens unit 20 is placed at the first position may be set to be different from the exposure time of the second image captured in a state in which the lens unit 20 is placed at the second position. For example, in consideration of the fading of chemiluminescence, the exposure time of the second image captured after the first image may be set to be longer than the exposure time of the first image.

Figure 9:
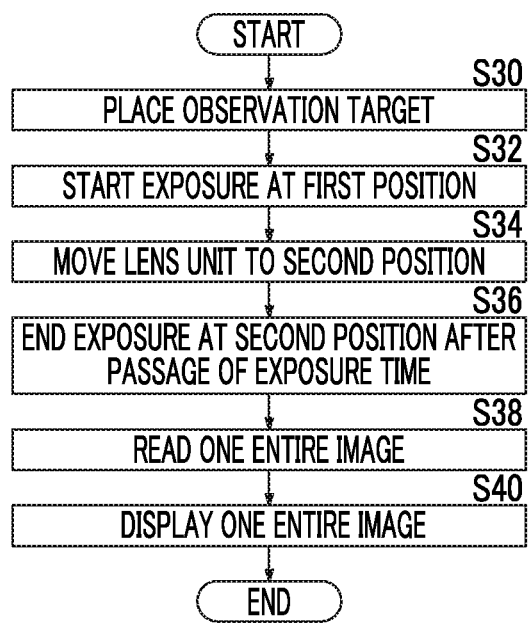
FIG. 9 is a flowchart illustrating an embodiment in which a lens unit is moved from the first position to the second position during a single exposure time.

In addition, although one entire image is formed and acquired by superimposing the first image captured in a state in which the lens unit 20 is placed at the first position and the second image captured in a state in which the lens unit 20 is placed at the second position in the image pickup system of the embodiment described above, another method of acquiring the entire image will be described below with reference to the flowchart shown in FIG. 9.

First, similar to the embodiment described above, the observation target S is placed on the observation target holding unit 30 (S30). Then, the user inputs an imaging start instruction using the input device 70, so that imaging is started.

Specifically, exposure of the detection unit 10 is started in a state in which the lens unit 20 is placed at the first position, and light transmitted through the SELFOC lens array 21 of the lens unit 20 is detected by the detection unit 10 (S32).

Then, without the first image being read from the detection unit 10 as in the embodiment described above, the cam 43 of the moving mechanism 40 rotates in response to a control signal output from the moving mechanism control unit 52, and accordingly the lens unit 20 moves in the Y direction to move to the second position (S34).

Then, light transmitted through the SELFOC lens array 21 in a state in which the lens unit 20 is placed at the second position is detected by the detection unit 10, and the exposure is ended after the passage of exposure time set in advance (S36). That is, exposure in a state in which the lens unit 20 is placed at the first position and exposure in a state in which the lens unit 20 is placed at the second position are continuously performed without performing the reading of an image. As a result, the entire image of the observation target S is captured by the detection unit 10.

Then, the entire image of the observation target S is read from the detection unit 10 in response to a control signal output from the control unit 51, and the read entire image is output to the display control unit 54 (S38). The display control unit 54 displays the entire image of the observation target S on the display device 60 (S40).

As described above, the entire image may be acquired by moving the lens unit 20 to the second position from the first position during a single exposure time set in advance.

In addition, the lens unit 20 may be made to reciprocate between the first position and the second position during a single exposure time. As a method of reciprocation, for example, the lens unit 20 may be made to reciprocate at a cycle of 1 Hz during the exposure time of 10 minutes.

In addition, although the lens unit 20 is made to move from the first position to the second position in the embodiment described above, the observation target holding unit 30 and the detection unit 10 may be moved in the Y direction instead of moving the lens unit 20. In addition, the lens unit 20 and the observation target holding unit 30 and the detection unit 10 may be moved in opposite directions in the Y direction.

Figure 10:
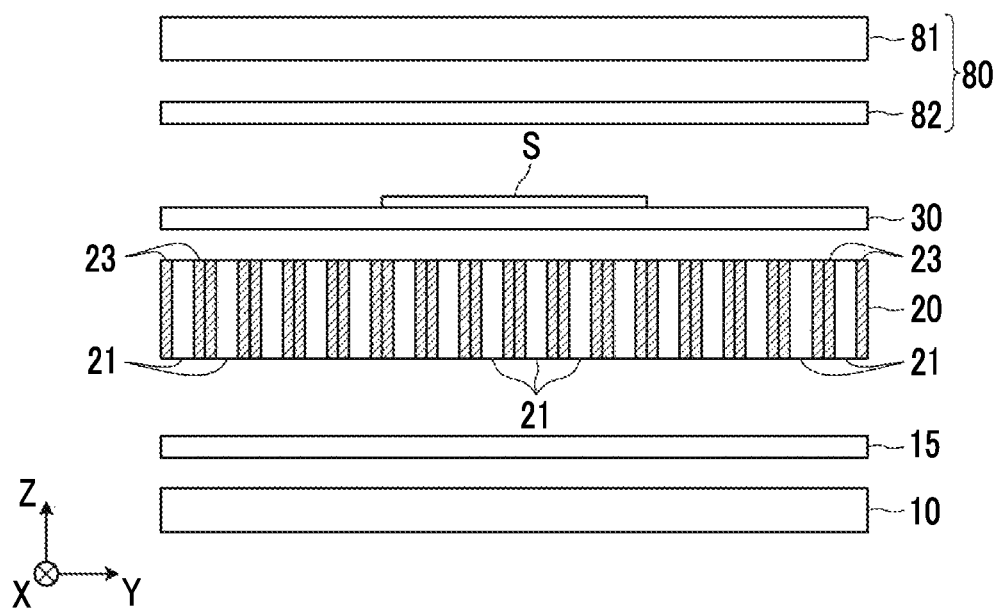
FIG. 10 is a diagram showing the schematic configuration of an embodiment to detect the fluorescence of an observation target.

Next, an embodiment will be described in which excitation light is emitted to the observation target S and fluorescence emitted from the observation target S by the emission of the excitation light is detected by the detection unit 10. FIG. 10 is a diagram showing the schematic configuration of an embodiment to detect the fluorescence of the observation target S. In the present embodiment, an excitation light emission unit 80 and an excitation light cut filter 15 are provided in addition to the configuration of the embodiment described above.

The excitation light emission unit 80 emits excitation light to the observation target S. The excitation light emission unit 80 includes an excitation light source 81 and an excitation light filter 82.

As the excitation light source 81, it is possible to use alight source in which light emitting diodes (LEDs) that emit excitation light are arranged in a two-dimensional manner, for example. The excitation light source 81 is not limited to such a configuration, and any configuration capable of realizing surface emission of excitation light may be used. In addition, a white light source that emits white light may be used as the excitation light source 81.

The excitation light filter 82 is provided between the excitation light source 81 and the observation target holding unit 30, and transmits light in a wavelength range set in advance, which includes the center wavelength of the excitation light, and inhibits the transmission of light having a wavelength outside the wavelength range.

The excitation light cut filter 15 is provided between the observation target holding unit 30 and the detection unit 10, and inhibits the incidence of excitation light to the detection unit 10. By providing the excitation light cut filter 15, it is possible to suppress the generation of noise due to incidence of excitation light to the detection unit 10. Therefore, it is possible to improve the S/N of the image of the observation target S.

In the present embodiment, the excitation light emitted from the excitation light emission unit 80 is emitted to the observation target S, and the fluorescence emitted from the observation target S by the emission of the excitation light is transmitted through the SELFOC lens array 21 of the lens unit 20 and is detected by the detection unit 10.

Then, similar to the embodiment described above, a first fluorescence image is captured in a state in which the lens unit 20 is placed at the first position, a second fluorescence image is captured in a state in which the lens unit 20 is placed at the second position, and the first and second fluorescence images are input to the image forming unit 53.

The first and second fluorescence images input to the image forming unit 53 are superimposed to form an entire fluorescence image, and the entire fluorescence image is displayed on the display device 60 by the display control unit 54.

Also in the embodiment to capture a fluorescence image, exposure in a state in which the lens unit 20 is placed at the first position and exposure in a state in which the lens unit 20 is placed at the second position are continuously performed without performing the reading of a fluorescence image.

The configuration of the excitation light emission unit 80 is not limited to the configuration in which light is emitted from above the observation target S as shown in FIG. 10, and a configuration in which light is emitted from diagonally below the observation target S as shown in FIG. 11 may be adopted. In the configuration shown in FIG. 11, the excitation light source 81 and the excitation light filter 82 are integrally formed, and the excitation light emission unit 80 that is integrally formed is disposed obliquely downward on both sides of the observation target holding unit 30. Excitation light emitted to the observation target holding unit 30 reaches the observation target S after being transmitted through or reflected from the inside of the observation target holding unit 30, thereby being mined to the observation target.

In addition, also in the embodiment to detect the fluorescence described above, the observation target holding unit 30 and the detection unit 10 may be moved in the Y direction instead of moving the lens unit 20. In addition, the lens unit 20 and the observation target holding unit 30 and the detection unit 10 may be moved in opposite directions in the Y direction.

In the embodiment shown in FIG. 10 or 11 in which fluorescence emitted from the observation target S by the emission of excitation light is detected by the detection unit 10, stimulable emission light that is emitted from a phosphor sheet may be detected by the detection unit 10 using a phosphor sheet including a stimulable phosphor layer as the observation target S. For example, the phosphor sheet receives a radiation transmitted through a subject and records a radiological image of the subject thereon. In addition, a stimulable phosphor is excited by the emission of excitation light, and the phosphor sheet emits stimulable emission light corresponding to the radiological image.

In the case of detecting the stimulable emission light emitted from the phosphor sheet described above, in the embodiment shown in FIG. 10 or 11, excitation light is uniformly emitted to the phosphor sheet. Accordingly, for example, when the lens unit 20 is placed at the first position, the excitation light is emitted not only to a position on the phosphor sheet corresponding to each SELFOC lens array 21 but also to a position on the phosphor sheet corresponding to the lens holding unit 23. That is, excitation occurs up to the area of the phosphor sheet that is to be detected when the lens unit 20 is placed at the second position. For this reason, it is not possible to detect the fluorescence of the area.

Figure 13:
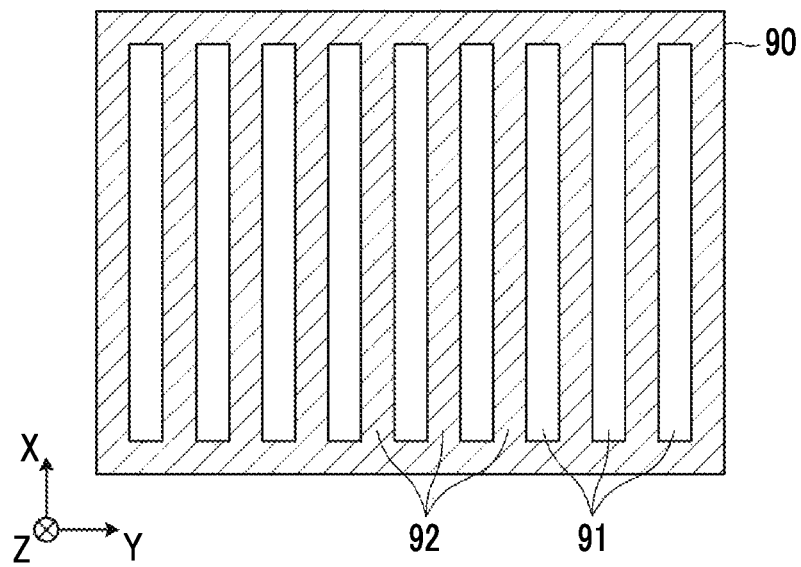
FIG. 13 is a plan view showing the schematic configuration of a shutter unit in the embodiment shown in FIG. 12.

Therefore, as shown in FIG. 12, a shutter unit 90 may be provided between the excitation light emission unit 80 and the observation target S. As shown in FIG. 13, in the shutter unit 90 of the present embodiment, a plurality of openings 91 extending in the X direction are provided in the Y direction for a light shielding member 92 that has flat plate shape and is formed of a material that blocks excitation light. A plurality of openings 91 are provided at intervals corresponding to the distance between the center axes of the SELFOC lens arrays 21, and the width of the opening 91 in the Y direction is set to a width equal to or less than the width of the SELFOC lens array 21 in the Y direction.

The shutter unit 90 is moved in the Y direction by a shutter moving mechanism 95. As the shutter moving mechanism 95, for example, a mechanism configured to include a support member, a spring member, and a cam can be used, similar to the moving mechanism 40 for moving the lens unit 20 in the embodiment described above. However, the shutter moving mechanism 95 is not limited to this configuration, and other known mechanisms can be used as long as it is possible to move the shutter unit 90 in the Y direction.

In addition, the shutter moving mechanism 95 is controlled according to a control signal output from the moving mechanism control unit 52. The moving mechanism control unit 52 controls the shutter moving mechanism 95, so that the shutter unit 90 is moved in synchronization with the movement of the lens unit 20. The moving distance of the shutter unit 90 in the Y direction is the same as the moving distance of the lens unit 20 in the Y direction.

In addition, by moving the shutter unit 90 in synchronization with the movement of the lens unit 20 as described above, it is possible to prevent excitation light from being emitted not only to a position on the phosphor sheet corresponding to each SELFOC lens array 21 but also to a position on the phosphor sheet corresponding to the lens holding unit 23 when the lens unit 20 is placed at the first position.

Figure 14:
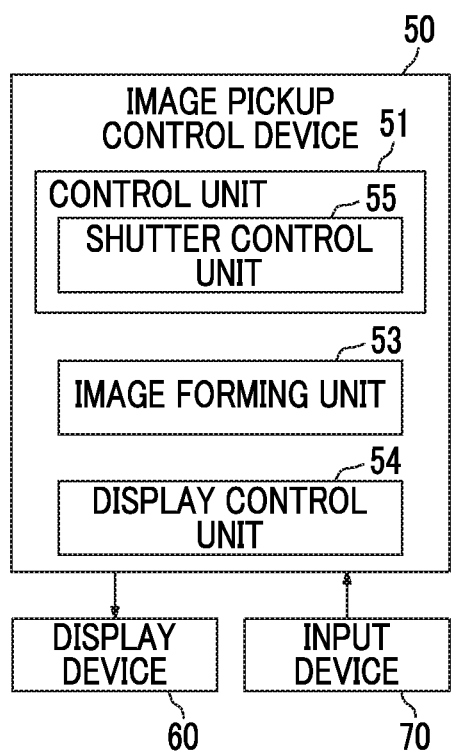
FIG. 14 is a block diagram showing the schematic configuration of an image pickup control device in a case where the shutter unit is formed by a spatial light modulator, such as a liquid crystal shutter.

The shutter unit 90 is not limited to the mechanical structure described above, and a spatial light modulator, such as a liquid crystal shutter, may be used as the shutter unit 90. In this case, as shown in FIG. 14, the control unit 51 of the image pickup control device 50 includes a shutter control unit 55 that controls the shutter unit 90 having a spatial light modulator. The shutter control unit 55 outputs a control signal to the shutter unit 90 to switch the position of the opening. Opening position switching in the case of forming the shutter unit 90 using a spatial light modulator may be performed in synchronization with the movement of the lens unit 20, similar to the movement of the shutter unit 90 having a mechanical configuration described above. By using the spatial light modulator or the like as the shutter unit 90 as described above, it is possible to omit a mechanical structure for moving the shutter unit 90. Therefore, it is possible to miniaturize the device.

In the case of moving the opening position of the shutter unit 90 and the lens unit 20 in the Y direction as described above, the emission of excitation light from the excitation light emission unit 80 may be stopped during the movement. In this manner, it is possible to further prevent the emission of excitation light to the position on the phosphor sheet corresponding to the lens holding unit 23.

Also in the embodiment shown in FIG. 10 or 11 in which the shutter unit 90 is not provided, it is preferable to stop the emission of excitation light from the excitation light emission unit 80 while moving the lens unit 20 or the observation target holding unit 30 and the detection unit 10 in the Y direction.

What is claimed is:

1. An image pickup device, comprising:
an observation target holding unit that holds an observation target;
a detection unit in which detection elements for detecting light emitted from the observation target are arranged in a two-dimensional manner;
a lens unit which is disposed between the observation target holding unit and the detection unit and in which a plurality of lens arrays, each of which includes a plurality of refractive index distribution type lenses that are linearly arranged, are arranged in a direction perpendicular to an arrangement direction of the refractive index distribution type lenses and a lens holding unit that blocks the light is provided between the lens arrays;

a moving mechanism that moves the lens unit or the observation target holding unit and the detection unit in the perpendicular direction; and a moving mechanism control unit that controls the moving mechanism, wherein the moving mechanism control unit controls the moving mechanism such that the lens unit or the observation target holding unit and the detection unit are moved to a second position from a first position, and the second position is a position when the lens array of the lens unit after the movement is disposed at a position facing a detection surface of the detection unit shielded by the lens holding unit when the lens unit is disposed at the first position.

2. The image pickup device according to claim 1, wherein a moving distance from the first position to the second position is shorter than a distance between center axes of the lens arrays disposed adjacent to each other in the perpendicular direction.

3. The image pickup device according to claim 2, wherein a plurality of the second positions are set in the perpendicular direction.

4. The image pickup device according to claim 3, further comprising:

an image forming unit that forms one image by superimposing a first image detected at the first position by the detection unit and a second image detected at the second position by the detection unit.

5. The image pickup device according to claim 2, further comprising:

an image forming unit that forms one image by superimposing a first image detected at the first position by the detection unit and a second image detected at the second position by the detection unit.

6. The image pickup device according to claim 2, wherein the moving mechanism control unit moves the lens unit or the observation target holding unit and the detection unit to the second position from the first position during a single exposure time set in advance.

7. The image pickup device according to claim 1, wherein a plurality of the second positions are set in the perpendicular direction.

8. The image pickup device according to claim 3, further comprising:

an image forming unit that forms one image by superimposing a first image detected at the first position by the detection unit and a second image detected at the second position by the detection unit.

9. The image pickup device according to claim 7, wherein the moving mechanism control unit moves the lens unit or the observation target holding unit and the detection unit to the second position from the first position during a single exposure time set in advance.

10. The image pickup device according to claim 1, further comprising:

an image forming unit that forms one image by superimposing a first image detected at the first position by the detection unit and a second image detected at the second position by the detection unit.

11. The image pickup device according to claim 1, wherein the moving mechanism control unit moves the lens unit or the observation target holding unit and the detection unit to the second position from the first position during a single exposure time set in advance.

12. The image pickup device according to claim 11, wherein the moving mechanism control unit makes the lens unit or the observation target holding unit and the detection unit reciprocate between the first and second positions during the single exposure time.

13. The image pickup device according to claim 1, further comprising:

an excitation light emission unit that emits excitation light to the observation target, wherein the detection unit detects fluorescence emitted from the observation target due to emission of the excitation light.

14. The image pickup device according to claim 13, further comprising:

an excitation light filter that is provided between the excitation light emission unit and the observation target holding unit and that transmits light in a wavelength range set in advance, which includes a center wavelength of the excitation light, and inhibits transmission of light having a wavelength outside the wavelength range.

15. The image pickup device according to claim 13, further comprising:

an excitation light cut filter that is provided between the observation target holding unit and the detection unit and inhibits incidence of the excitation light to the detection unit.

16. The image pickup device according to claim 13, further comprising:

a shutter unit which is provided between the excitation light emission unit and the observation target and in which openings are provided at intervals corresponding to a distance between center axes of the lens arrays for a light shielding member for blocking the excitation light.

17. The image pickup device according to claim 16, further comprising:

a shutter moving mechanism that moves the shutter unit in the perpendicular direction, wherein the moving mechanism control unit controls the shutter moving mechanism such that the shutter unit is moved in synchronization with movement of the lens unit.

18. The image pickup device according to claim 16, further comprising:

a shutter control unit that switches positions of the openings of the shutter unit in synchronization with movement of the lens unit.

19. The image pickup device according to claim 13, wherein the excitation light emission unit stops emission of the excitation light during movement of the lens unit or the observation target holding unit and the detection unit.

20. An image pickup method of detecting light emitted from the observation target held by the observation target holding unit by the detection unit including the detection elements arranged in a two-dimensional manner using the image pickup device according to claim 1, the method comprising:

moving the lens unit, which is disposed between the observation target holding unit and the detection unit and in which the plurality of lens arrays, each of which includes the plurality of refractive index distribution type lenses that are linearly arranged, are arranged in the direction perpendicular to the arrangement direction of the refractive index distribution type lenses and the lens holding unit that blocks the light is provided between the lens arrays, or the observation target holding unit and the detection unit in the perpendicular direction such that the lens unit or the observation target holding unit and the detection unit are moved to the second position from the first position,
wherein the second position is the position when the lens array of the lens unit after the movement is disposed at the position facing the detection surface of the detection unit shielded by the lens holding unit when the lens unit is disposed at the first position.

* * * * *